United States Patent [19]

Löser

[11] Patent Number: 5,918,593
[45] Date of Patent: Jul. 6, 1999

[54] ULTRASONIC ATOMIZER FOR RESPIRATION SYSTEMS

[75] Inventor: Ralf-Ernst Löser, Lübeck, Germany

[73] Assignee: Drägerwerk AG, Lübeck, Germany

[21] Appl. No.: 08/974,265

[22] Filed: Nov. 19, 1997

[30] Foreign Application Priority Data

Jun. 20, 1997 [DE] Germany .............................. 197 26 110

[51] Int. Cl.⁶ .................................................. A61M 11/00
[52] U.S. Cl. ................................ 128/200.16; 128/203.12; 128/204.18
[58] Field of Search .......................... 128/200.16, 203.12, 128/200.22, 200.23, 204.23, 204.18, 204.25

[56] References Cited

U.S. PATENT DOCUMENTS

| | | | |
|---|---|---|---|
| 4,976,259 | 12/1990 | Higson et al. | 128/200.18 |
| 5,063,922 | 11/1991 | Hakkinen | 128/200.16 |
| 5,152,457 | 10/1992 | Burwell | 239/102.2 |
| 5,443,059 | 8/1995 | Koch et al. | 128/200.16 |

FOREIGN PATENT DOCUMENTS

| | | |
|---|---|---|
| 43 00 880 C2 | 3/1996 | Germany . |
| WO 93/09881 | 5/1993 | WIPO . |

*Primary Examiner*—John G. Weiss
*Assistant Examiner*—Charles W. Anderson
*Attorney, Agent, or Firm*—McGlew and Tuttle

[57] ABSTRACT

An ultrasonic atomizer for respiration systems, which is integrated in the breathing gas line from and to the patient via two connections. The ultrasonic atomizer is in a gas flow connection with the atomizer chamber to which an aerosol is admitted by a piezo vibrating element for the inhalation via a nonreturn valve. The arrangement bridges over the atomizer chamber for the exhalation via a second nonreturn valve by means of a second, spatially separated gas flow path.

18 Claims, 2 Drawing Sheets

ULTRASONIC ATOMIZER FOR RESPIRATION SYSTEMS

FIELD OF THE INVENTION

The present invention pertains to an ultrasonic atomizer for respiration systems.

BACKGROUND OF THE INVENTION

Atomizers have hitherto been used to administer drugs into the lungs of artificially respirated patients by means of correspondingly generated aerosols, which are added to the inhaled air. The administration is usually performed by inserting a pneumatic atomizer into the inspiration tube leading from the respirator to the patient connection, the so-called Y-piece. The breathing gas flowing through the atomizer during the inhalation phase is enriched with aerosol, and the breathing gas is also mixed with the propellant gas of the atomizer due to the pneumatic drive of the atomizer. Special measures must therefore be taken to guarantee the desired oxygen concentration for the patient. A prior-art ultrasonic atomizer inserted at the same point is free from this drawback. Nevertheless, it is disadvantageous that the aerosol is generated at a point relatively remote from the patient. Part of the drug aerosol precipitates in the tube system on its way to the patient connection; more losses occur, especially in the case of continuous atomization without interruption, e.g., due to the propellant gas flow, which flows unused into the exhalation line, or due to the increased precipitation because of lack of removal of the aerosol.

The loss due to the escape of unused gas-aerosol mixture reaches up to 90%, and sometimes even more, especially in modes of operation needed in pediatric and especially neonatological applications. The distortion of the oxygen concentration due to the propellant gas flow is also unacceptable in this field of application. The arrangement of prior-art drug atomizers near the patient between the Y-piece and the tube connector is also impossible because of the additional dead space volume, which may be several times the tidal volume in the case of pediatric and neonatological applications. In addition, the exhaled gas would also be enriched with aerosol in such a case, or the atomizer would have to be synchronized with the breathing cycle in a complicated manner.

DE 43 00 880 C2 describes an arrangement, which is to solve these problems by an ultrasonic atomizer located directly before the tube in the Y-piece being supplied, synchronously with the breathing, with a small amount of the substance to be atomized during the inhalation via a nozzle, and by this substance being atomized by the atomizer directly into the tube.

The drawback of this arrangement is, on the one hand, that triggering and a tidal volume-dependent metering of the amount of liquid is necessary, and, on the other hand, that no aerosol selection is performed. The latter means that droplets of all sizes formed flow to the patient. This results in the deposition of considerable amounts in the tube and in the upper part of the respiratory tract because of excessively large droplets. In addition, complete atomization of the amount of liquid injected onto the atomizer is not guaranteed, so that so much excess will gradually collect in the course of a plurality of breathing cycles that the atomization will come to a standstill. As an inherent feature of the system, the temperature of the atomizer surface will increase, as a result of which sensitive, protein-containing substances will be destroyed.

SUMMARY AND OBJECTS OF THE INVENTION

The primary object of the present invention is to propose an arrangement, with which an aerosol can be generated and mixed with the inhaled breathing gas flow close to the patient, i.e., directly before the patient tube, and wherein the exhaled breathing gas flow is extensively free from drug aerosol. In addition, synchronization with the respirator shall not be necessary. Moreover, the drop size shall be in a therapeutically effective spectrum, so that a high rate of deposition will be reached in the desired areas of the lungs. Even difficult-to-atomize substances, which are sensitive to high temperatures because of their composition, shall be able to be atomized. The residual amount remaining in the atomizer shall be very small, i.e., markedly less than one milliliter, in order to make possible the efficient use even of very expensive drugs.

According to the invention, an ultrasonic atomizer for respiration systems is provided wherein the ultrasonic atomizer is integrated in the only breathing gas line from and to the patient via two connections and is in a gas flow connection with the atomizer chamber to which aerosol is admitted by means of a said piezo vibrating element via a nonreturn valve for the inhalation, on the one hand, and, on the other hand, it bridges over the atomizer chamber for the exhalation via a second nonreturn valve by means of a second, spatially separated gas flow path.

The atomizer chamber preferably has a closable channel for receiving the drug to be atomized by means of the piezo vibrating element. The atomizer chamber preferably has a lateral opening for the entry of the breathing gas and a nozzle-like discharge opening in the form of an impactor in the upper part for the breathing gas outlet.

A baffle plate may be used to set the size distribution of the atomized aerosol. This baffle plate may be arranged in the atomizer chamber in the path of the gas flow.

The nonreturn valves, the connections, and the breathing gas flow channels, as well as the upper part of the atomizer chamber are preferably arranged in a breathing gas channel and valve block, and the complementary, lower part of the atomizer chamber is preferably arranged in a the atomizer chamber block. The atomizer chamber is preferably electrically and mechanically connected in a ring-shaped manner to the piezo vibrating element via a contact plate of the piezo holder, which contact plate is designed as a metal contact surface. The atomizer chamber block may consist of a metal with good thermal conductivity, especially aluminum. The drug in the atomizer chamber is preferably cooled via Peltier elements arranged at the connection surface from the outside with the cooling bodies and with a fan arranged under the piezo vibrating element.

One essential advantage of the present invention in terms of low costs and ready availability of the components used is that parts of a prior-art, special manual ultrasonic atomizer are used, which is optimized for a high atomization output at low energy consumption. Essential components are the piezo vibrating element, its mechanical adaptation to the atomization chamber, and the energizing electronic unit belonging to it. Reference is made expressly in this connection to the Patent Publication WO 93/09881, in which the above-mentioned manual ultrasonic atomizer is described in detail. The drop size spectrum generated by this atomizer is optimally coordinated with respect to deposition in the lungs.

The various features of novelty which characterize the invention are pointed out with particularity in the claims

DESCRIPTION OF THE PREFERRED EMBODIMENT

Figure 1:
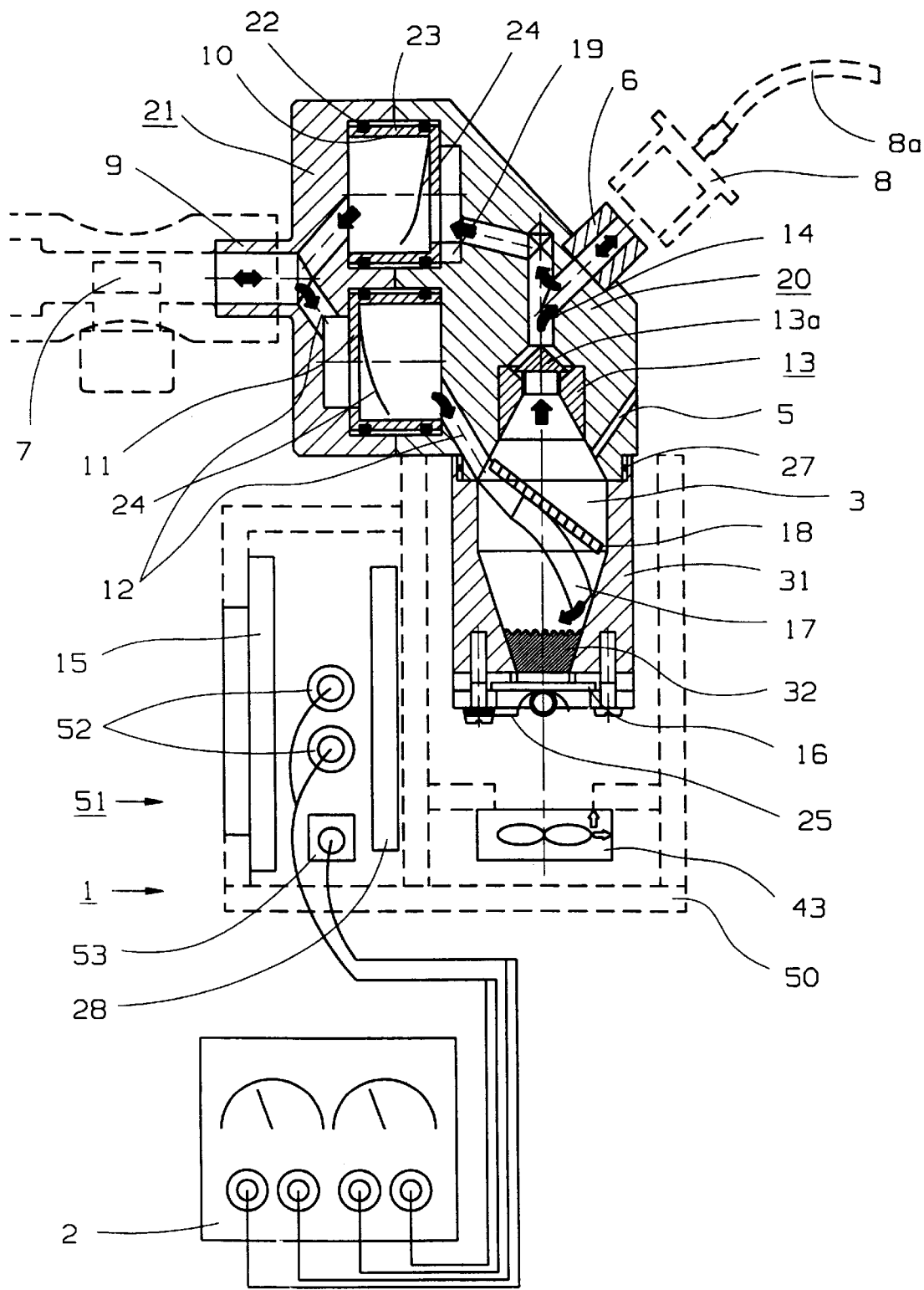
FIG. 1 is a partially schematic sectional view of the ultrasonic atomizer system according to the invention.

Referring to the drawings in particular, one exemplary embodiment of the present invention will be explained on the basis of FIGS. 1 and 2. The arrows indicate the direction (s) of flow and the exhaled breathing gas flow through the ultrasonic atomizer 1 according to the present invention. The overall arrangement of the ultrasonic atomizer 1 according to the present invention shown in FIG. 1 comprises, besides the above-mentioned components, a metallic atomizer chamber block 31 with the atomizer chamber 3 proper inside it. The atomizer also includes a breathing gas channel and valve block 20, 21, and a Peltier cooling device 4, 41, 42. The task of the breathing gas and valve block 20, 21 is to establish the connection between the tube connector 8 and the Y-piece or the flow sensor 7 and to lead the inhaled gas flow through the atomizer chamber 3 in a passive manner, while the exhaled gas flow is led past the chamber through a bypass channel 14. This function is achieved by two nonreturn valves 10, 11. Furthermore, this block is also designed such that the aerosol that may precipitate in the inhalation channels during use returns into the atomizer chamber 3. The connections 6, 9 for the tube connector 8 and the Y-piece with the flow sensor 7 inserted between them, which is indicated by a broken line, and the channels used jointly by the inhaled and exhaled gas flows, are designed such that they together lead to a minimal additional dead space of up to about 1 mL. A separate small, closable channel 5 makes it possible to add more drug 32 from the outside, without having to open the atomizer chamber 3. The breathing gas channel and valve block 20, 21 is designed as a divisible block, so that the individual parts can be easily removed for cleaning.

The drug 32 would also be heated slightly in this atomizer, which is unfavorable especially in the case of so-called surfactants, i.e., surface-active substances. The atomizer chamber 3 is therefore cooled, preferably with one or two Peltier elements 4 (See FIG. 2). Since the oversized drops precipitate on the walls of the atomizer chamber 3 during the atomization process and they return to the piezo vibrating element 16, cooling of this element is also guaranteed by this liquid circulation. The use of the ultrasonic atomizer 1 according to the present invention offers the advantage that the composition of the patient gas does not change. Using the atomizer being described, it is possible to generate drug aerosol close to the patient. Positioning directly before the patient tube 8a is possible due to the extremely small ventilatory dead space. The advantage of this is that the patient tubes as well as the expiration valve are no longer contaminated with drug aerosol. This is especially advantageous when the gas volume flow measurement (flow measurement), which is distorted or is even made impossible by the aerosol in the case of prior-art atomizers, is performed close to the patient. Since the atomizer described is positioned between the flow sensor 7 and the patient, the breathing gas flows through the flow sensor 7 free from aerosol during the inhalation and only with the low aerosol concentration flowing back from the patient during the exhalation. It is not necessary to perform an inhalation/exhalation switchover with triggering means. The separation of the inspiratory and expiratory gas flow with low-resistance nonreturn valves 10, 11 makes it possible for the inspiratory gas flow to be enriched with aerosol and for the expiratory gas flow to remain very extensively free from aerosol, even though the aerosol is being generated continuously in the atomizer chamber 3. The aerosol is enriched in the atomizer chamber 3 during the exhalation, so that the highest concentration is present at the beginning of the next inhalation, i.e., in the case of the volume fraction that penetrates most deeply into the lungs. The aerosol concentration is comparatively lower at the end of the inspiration, which is a definitely desirable effect, because this volume stops in the upper dead space and thus it escapes unused during the exhalation. It was achieved due to the design of the atomizer chamber 3 and of the breathing gas channel and valve block 20, 21 that aerosol drops that precipitate on the walls flow back into the lower area of the atomizer chamber 3 containing the drug 32 in order to continue to be available for the atomization process. Thus, considerably less than 1 mL of drug 32 is left in the atomizer chamber 3 at the end of the atomization. On the other hand, the total amount to be atomized is quasi unlimited, because the drug 32 can be introduced through a closable refilling opening designed as a channel 5 during the operation. The Peltier cooling device 4, 41, connected to the atomizer chamber 3 compensates the increase in the temperature of the drug 32 which is associated with the ultrasonic atomization. It is thus also possible to atomize sensitive substances without these substances being damaged by thermal effects. The inner walls of the atomizer chamber 3 in the atomizer chamber block 31 were made as steep walls in order to support the desired flowing back of the drug 32 onto the piezo vibrating element 16.

Figure 2:
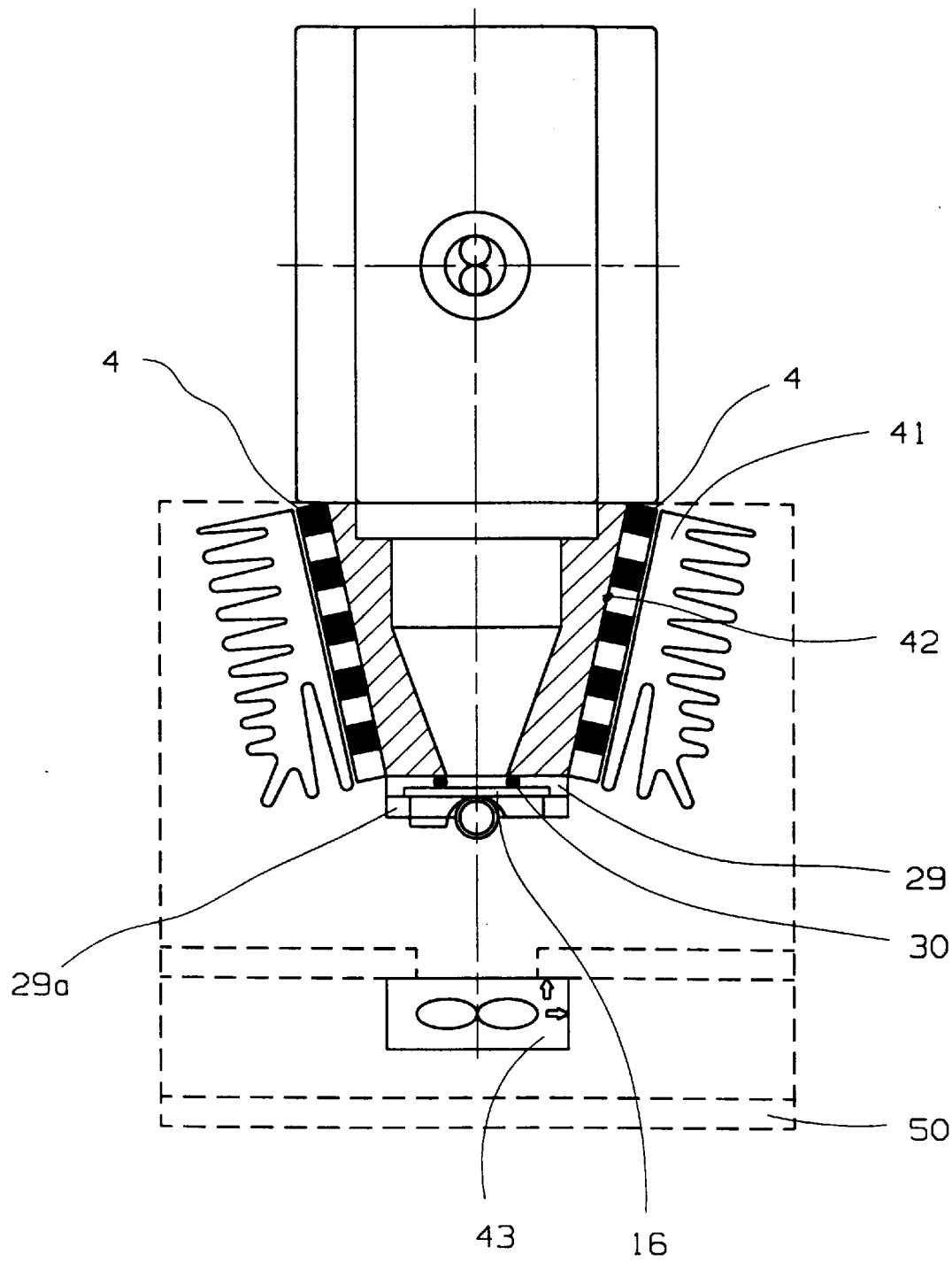
FIG. 2 is a partially schematic sectional view of the ultrasonic atomizer of FIG. 1, taken from a different direction.

As can be recognized from the representation in FIG. 2, the connection of two Peltier elements 4, on the one hand, and the requirement that the volume of the atomizer chamber 3 be small, on the other hand, are taken into account by the design measures taken in connection with the atomizer chamber block 31. It was achieved as a result that a comparatively small amount of drug 32 of less than about 1 mL is sufficient to wet the piezo vibrating element 16, as is needed for the operation. Furthermore, the compressible volume of the atomizer was reduced by these measures, and the effect on the respirator was kept as slight as possible as a result. The atomizer chamber block 31 was made of aluminum, because this material has good thermal conductivity and the heat originating from the piezo vibrating element 16 can thus be better dissipated by the Peltier elements 4. The outer surfaces 42 of the atomizer chamber block 31 for connecting the Peltier elements 4 have a small surface roughness (Rz 10), which is sufficient for the contact with the ceramic surface of the cooling elements via thermocontact paste. The cooling bodies 41 stand very steeply due to the 10° inclination of the surfaces to the vertical, as a result of which the dimension of the atomizer housing can be kept as small as possible and it facilitates the flow of the air flow from the fan 43 around the cooling bodies 41. The underside of the atomizer chamber block 31 was designed for setting the piezo vibrating element 16. It accommodates both the piezo vibrating element 16 and the contact and sensor parts 25 needed for contacting and temperature monitoring.

The valve block 21 contains the connections 6, 9 for the Y-piece or the intercalated flow sensor 7 and the tube connector 8, two nonreturn valves 10, 11 for switching over between inspiratory flow and expiratory flow, channels 12, a bypass channel 14 for guiding the breathing gas flows, as well as the cover for the atomizer chamber 3. The valve block 21 in the exemplary embodiment being described is optimized for application in neonatology. The connection diameters and channel cross sections may be adapted for other fields of use. The dimensions of the channels 12, of the bypass channel 14, as well as of the top side of the atomizer chamber 3 were selected with the aim of minimizing the ventilatory dead space. The shape of the channel on the inspiration side permits the inhaled air to flow in at the chamber wall. As a result, the aerosol is pressed upward on the side opposite the intake and can flow to the patient tube 8a via the vertical part of the bypass channel 14 in the breathing gas channel block 20. An impactor 13, which can be screwed in and will be described in detail below, is integrated in this vertical part of the bypass channel 14. The exhalation side has, before the setting of the expiratory nonreturn valve 10, a drainage groove 19, which is used as a water trap to protect the nonreturn valve 10 from moisture. The connection 6 was designed with an external cone with a diameter of 11 mm. This nonstandardized connection 6 offers the advantage that it fills out the inner hollow space of the tube connector 8 and thus reduces the ventilatory dead space. The breathing gas channel and valve block 20, 21 is connected to the atomizer chamber block 31 via a circular fit, which is sealed with an O-ring 27. The upper part of the atomizer chamber 3 is integrated by this division in the right-hand part of the breathing gas channel and valve block 20, 21. This part of the breathing gas channel and valve block 20, 21 has steep and polished surfaces in order to reduce the adhesion of drops of drug to allow drops deposited there to flow back onto the piezo vibrating element 16. The impactor 13 is located in the inspiratory part of the bypass channel 14 between the atomizer chamber 3 and the connection 6. It contracts in the direction of flow from 14 mm to 5 mm in diameter. The aerosol drops are accelerated by the nozzle effect thus achieved. The response of larger drops during a change in the direction of flow is slower because of the higher inertia of masses of such drops. If the direction of flow of drops accelerated through a nozzle is deflected by a baffle plate 18, the larger drops are separated on the surface of the impactor disk 13a. The baffle plate 18 may completely replace the impactor 13 in an extreme case. As a result, particles which are too large for the aerosol therapy are separated during the operation of the ultrasonic atomizer 1. The size of the drops for the therapy can be influenced by varying the size of the impactor disk 13a or of the baffle plate 18. The impactor disk 13a is designed as a cone on the side facing away from the flow in order to allow the drops that may still be separated behind the impactor 13 to flow back into the atomizer chamber 3. The art nonreturn valves 10, 11, which are designed as diaphragm valves, were prepared for the use in the ultrasonic atomizer 1 such that only the volume needed for the function and the valve seat are present. Their setting in the ultrasonic atomizer 1 is located between the cover and the respiration connection. Their seat is sealed at the external diameter with a fit and an O-ring 22. The flow through the nonreturn valves 10, 11 is such that the flow is directed toward the point of the silicone diaphragm 24 located farthest away from the support point on the circumference. The longest lever action resulting from this leads to the minimization of the pressures that are needed to open the nonreturn valves 10, 11. Both the inspiration valve and the expiration valve (nonreturn valves 10, 11) are connected in the connection part of the respiration side with the connection 9. The dimensions of the fit are selected to be such that disassembly/assembly for cleaning is possible even without tools by replacing the silicone diaphragm 24, without having to accept the risk of gap losses. The connection to the respirator is with an ISO 15 external cone, so that the use of a flow sensor 7 with small dead space is possible. The additional ventilatory dead space and the compressible volume formed in the connection part is kept so small by the holes with a diameter of 5 mm for the inhalation and expiration channels that the overall dead space required, about one mL, is not exceeded. The largest compressible space is formed in this component by the connection of the nonreturn valves 10, 11 and cannot be selected to be smaller because of the design constraints. The piezo vibrating element 16 has an energy supply and the control unit 28 indicated in outlines to ensure its function. The contacts 25 and the connection 29 to the atomizer chamber 3 according to the present invention were suitably adapted. Since the piezo vibrating element 16 consists of ceramic, it is very brittle and tends to break under mechanical stresses. The piezo vibrating element 16 is therefore mounted on an O-ring 30 on the underside of the atomizer chamber 3, see FIG. 2. It was ensured by selecting a sufficient clearance that the piezo vibrating element 16 cannot be tensioned during the assembly with the contact plate 29a. Such stresses could jeopardize the function of the piezo vibrating element, or they may even lead immediately to the breakage of the ceramic. The ring-shaped electric and mechanical connection of the piezo vibrating element 16 is via a contact plate 29a of the piezo holder designed as a brass contact surface.

Since the surfaces of the Peltier element 4 consist of a ceramic material, they are held by means of cable binders. This guarantees a uniform surface pressure on the entire connection surface 42. The inclination of preferably about 10° to the vertical, which is generated by the slope of the underside of the atomizer chamber, optimizes the course of the flow of the air arriving from the fan 43 around the Peltier elements 4 and the cooling bodies 41 arranged on their warm side. For better heat conduction, a thermocontact paste may be used on both the warm side with the contact surface to the cooling bodies 41 and the cold side with contact to the atomizer chamber 3. The losses in heat transmission resulting from the surface roughness are kept at a minimum as a result. A thin layer of silicone adhesive or similar materials may also be used instead of the thermocontact paste. A thermal and mechanical connection is thus obtained, which makes the cable binders unnecessary.

The piezo vibrating element 16 is controlled by a control unit 28 shown schematically. The fan 43 and the Peltier elements 4 are supplied with energy separately, so that the cooling can take place as needed, independently from the atomization. The housing 50 is used to separately accommodate the atomization unit and the control and power supply unit. This is necessary, because the moisture released during the atomization or cleaning of the atomizer must not get into the electronic unit under any circumstances. Another task of the housing 50 is to guide the flow of cooling air from the fan 43 over the cooling bodies 41. Without this guidance of the flow, the air would escape laterally from the cooling bodies 41, and heat would build up as a consequence between the cooling bodies 41. On its front side, the housing 50 has a rectangular opening 51 as a holder for the operating element 15 of the piezo control. The two pin-and-socket connections 52, 53 for the power supply of the Peltier elements 4, the piezo vibrating element 16 and the fan 43 are located in the left-hand side wall of the housing of the electronic unit. Finally, the housing 50 is used as a stand for the entire atomization unit on a flat surface. This housing 50 is designed such that a sufficient distance is guaranteed from the support surface for drawing in the cooling air for the fan 43.

The mode of operation of the entire device will be described below. It is optimized for use in neonatology in the exemplary embodiment being described here. The ultrasonic atomizer 1 is connected to the power supply unit 2 via the power cable. The power supply unit has two outputs that can be controlled independently from one another for the piezo vibrating element 16/fan 43 and the Peltier elements 4. To guarantee the best possible protection of the drug 32, the cooling is started before the atomizer chamber 3 is filled. An operating voltage of 6 V proved to be favorable for the particular Peltier elements 4 used in the experiments. A temperature of about 18° C. becomes established after about 4 minutes. The atomizer chamber 3 is filled with drug 32 either by means of a disposable syringe or a cannula with a maximum diameter of 1.6 mm or via an automatic supply from a reservoir, which is controlled by the control unit 28, e.g., via a metering pump, via the closable channel 5 intended for filling under the connection 6 to the patient. Consequently, more drug 32 can be introduced through this channel 5 when needed.

The preparation for the treatment begins with the connection of the ultrasonic atomizer 1 to the respiration system. The ultrasonic atomizer 1 is placed next to the patient and is inserted by opening the respiration system between the flow sensor 7 and the tube connector 8. Based on the design of the atomizer connections, this may happen on the respiration side and on the patient side, without the respiration having to be interrupted, because the entire procedure takes at most 2 seconds. The connections cannot be confused, because they fit the ultrasonic atomizer 1 in the correct direction of flow only.

Once the ultrasonic atomizer 1 has been connected, the air used for respiration is split inside it by the two nonreturn valves 10 and 11 into inhalation via the nonreturn valve 11 and exhalation via the nonreturn valve 10. The nonreturn valve 10 is closed during the inhalation phase and the air used for respiration flows through the nonreturn valve 11 and the channels 12 into the atomizer chamber 3 and from there to the patient through the impactor 13, the connection 6, the tube connector 8 and the patient tube 8a. Exhalation takes place when the overpressure in the respiration system is again reduced by the respirator. The air now flows from the lungs in the reverse direction through the patient tube 8a and the tube connector 8 and the connection 6 to above the impactor 13. The air is returned here to the respirator, not shown, through the vertical part of the bypass channel 14, the nonreturn valve 10 and the respiration-side connection 9. In this state of operation, i.e., with the piezo vibrating element 16 switched off, normal respiration takes place without the addition of aerosol. Since the drug 32 is already cooled in the atomizer chamber 3, the atomizer can be kept in this "state of waiting" over a rather long period of time without this leading to disadvantages for the subsequent therapy.

The drug treatment is begun when the start button on the operating element 15 of the atomizer is actuated and the aerosol generation begins in the atomizer chamber 3 as a result. A drug mist is thus continuously generated by the piezo vibrating element 16, and this mist is mixed with the breathing gas during the inhalation. The heat released from the vibrating piezo vibrating element 16 allows the temperature in the atomizer chamber 3 to rise as long as the amounts of heat introduced into and removed from the atomizer chamber 3 are equal. This stationary point was found at about 21° C. in the test runs and was able to be maintained for up to 1 hour. A longer atomization time is also quite possible should it be necessary for the therapy.

The air to be inhaled is introduced, e.g., with a silicone tube 17 at the rear wall of the atomizer chamber 3. As a result, the atomizer chamber 3 is swept from bottom to top and the aerosol is thus added to the air to be inhaled in a favorable manner. The air enriched with the drug aerosol enters the patient's lungs through the impactor 13 and the patient tube 8a. As an alternative, it is also possible to insert into the atomizer chamber 3 a baffle plate 18, which guides the air flow in the same manner as the tube 17, on the one hand, but, on the other hand, it retains larger aerosol drops already in the atomizer chamber 3 and thus it may make the impactor 13 superfluous. The exhalation takes place via the nonreturn valve 10. The only difference in the atomization operation is that drops of the drug may separate in the flow channels of the exhalation branch. These separations are due to flow losses or exhaled drops. If these are stuck already in the vertical part of the bypass channel 14 above the impactor 13, they flow back into the atomizer chamber 3 via the upper conical surface of the impactor disk 13a. It was also possible to observe during the operation that moisture may accumulate in the exhalation branch during prolonged operating time and at a higher atomizer output. However, this amount was always so small that it was caught in the drainage groove 19 before the nonreturn valve 10 at the latest and the valve never became wet or unable to operate during the operation. The silicone diaphragms 24 of the nonreturn valves 10, 11 still operate satisfactorily even in the wet state. Respiration cannot therefore be expected to be jeopardized even in the case of unfavorable operating parameters or inappropriate handling of the device.

The atomizer should be disassembled, cleaned and sterilized after use. All the parts that come into contact with the air used for respiration should be disinfected for this purpose. The sterilization is usually carried out under steam pressure at 134° C. The material of the part of the breathing gas channel and valve block 20, 21 forming the cover of the atomizer chamber 3, the respiration connection piece, the impactor 13 as well as the atomizer chamber 3, which is aluminum and PMMA, is selected to be such that it can be autoclaved. The O-rings 22 used as a seal as well as the silicone diaphragms 24 are disposable parts and are replaced after each treatment. To disassemble the atomizer, the pin-and-socket connections in the breathing gas channel and valve block 20, 21 as well as between the part forming the cover and the atomizer chamber 3 with the seal 27 are first loosened. The silicone diaphragms 24 and the O-rings 22 can then be removed from the valve seats 23 pulled off. The impactor 13 can be screwed out of the cover with a flat tool. The piezo vibrating element 16 may be cleaned together with the atomizer chamber 3, so that disassembly does not need to be performed.

While specific embodiments of the invention have been shown and described in detail to illustrate the application of the principles of the invention, it will be understood that the invention may be embodied otherwise without departing from such principles.

What is claimed is:

1. An ultrasonic atomizer arrangement for respiration systems, comprising:

a breathing gas line;

an ultrasonic atomizer integrated in said breathing gas line as the only breathing gas line from and to the patient via said two connections of the ultrasonic atomizer, said ultrasonic atomizer having an atomizer chamber with said breathing gas line in a gas flow connection with said atomizer chamber, said ultrasonic atomizer having a first nonreturn valve and a second nonreturn valve;

a piezo vibrating element connected to said atomizer chamber, for admitting aerosol to said breathing gas line via said nonreturn valve for inhalation, said atomizer chamber being bridged over for the exhalation via said second nonreturn valve by means of a second, spatially separated gas flow path.

2. An ultrasonic atomizer arrangement in accordance with claim 1, wherein said atomizer chamber has a closable channel for receiving a drug to be atomized.

3. The ultrasonic atomizer arrangement in accordance with claim 1, wherein said atomizer chamber has a lateral opening for the entry of breathing gas and a nozzle-like discharge opening in the form of an impactor in the upper part for the breathing gas outlet.

4. The ultrasonic atomizer arrangement in accordance with claim 1, further comprising:

a baffle plate, which is used to set the size distribution of the atomized aerosol, is arranged in said atomizer chamber in the path of the gas flow.

5. The ultrasonic atomizer arrangement in accordance with claim 1, wherein said nonreturn valves, said connections, and breathing gas flow channels defined by said ultrasonic atomizer, as well as an upper part of said atomizer chamber are arranged in a breathing gas channel and valve block, and a complementary, lower part of said atomizer chamber is arranged in an atomizer chamber block.

6. The ultrasonic atomizer arrangement in accordance with claim 5, wherein said atomizer chamber block is formed of a metal with good thermal conductivity.

7. The ultrasonic atomizer arrangement in accordance with claim 6, wherein said metal is aluminum or an aluminum alloy.

8. The ultrasonic atomizer arrangement in accordance with claim 1, wherein said atomizer chamber is electrically and mechanically connected in a ring-shaped manner to said piezo vibrating element via a contact plate of said piezo holder, which said contact plate is designed as a metal contact surface.

9. The ultrasonic atomizer arrangement in accordance with claim 1, further comprising:

peltier elements for cooling the drug in said atomizer chamber, said peltier elements being arranged at a connection surface;

cooling bodies; and a fan, said atomizer chamber being cooled form the outside via said peltier elements with said cooling bodies and with said fan arranged under said piezo vibrating element.

10. An ultrasonic atomizer for respiration systems, comprising:

a breathing gas line;

atomizer breathing gas line integration means defining two connections, two partially separated flow paths between said connections and an atomizer chamber, said breathing gas line forming the only breathing gas line from and to the patient via said two connections of said atomizer breathing gas line integration means, said atomizer chamber being in gas flow connection with one of said two partially separated flow paths, said breathing gas line integration means having a first nonreturn valve and a second nonreturn valve;

a piezo vibrating element connected to said atomizer chamber, for admitting aerosol to said breathing gas line via said one of said two partially separated flow paths and said first nonreturn valve for inhalation, said atomizer chamber being bridged over for the exhalation via said second nonreturn valve.

11. An ultrasonic atomizer in accordance with claim 10, wherein said atomizer chamber has a closable channel for receiving a drug to be atomized.

12. The ultrasonic atomizer in accordance with claim 10, wherein atomizer breathing gas line integration means has a lateral opening into said atomizer chamber for the entry of breathing gas and a nozzle-like discharge opening in the form of an impactor in the upper part for a breathing gas outlet.

13. The ultrasonic atomizer in accordance with claim 10, further comprising:

a baffle plate, which is used to set the size distribution of the atomized aerosol, is arranged in said atomizer chamber in the path of the gas flow.

14. The ultrasonic atomizer in accordance with claim 10, wherein said atomizer breathing gas line integration means includes a breathing gas channel and valve block connected to an atomizer chamber block, said nonreturn valves, said connections, and breathing gas flow paths, as well as an upper part of said atomizer chamber being arranged in said breathing gas channel and valve block, and a lower part of said atomizer chamber being arranged in said atomizer chamber block.

15. The ultrasonic atomizer in accordance with claim 14, wherein said atomizer chamber block is formed of a metal with good thermal conductivity.

16. The ultrasonic atomizer in accordance with claim 15, wherein said metal is aluminum or an aluminum alloy.

17. The ultrasonic atomizer in accordance with claim 10, wherein said atomizer chamber is electrically and mechanically connected in a ring-shaped manner to said piezo vibrating element via a contact plate of said piezo holder, which said contact plate is designed as a metal contact surface.

18. The ultrasonic atomizer in accordance with claim 10, further comprising:

peltier elements for cooling the drug in said atomizer chamber, said peltier elements being arranged at a connection surface;

cooling bodies; and a fan, said atomizer chamber being cooled form the outside via said peltier elements with said cooling bodies and with said fan arranged under said piezo vibrating element.

* * * * *